(12) United States Patent
Ebata et al.

(10) Patent No.: US 6,596,898 B2
(45) Date of Patent: *Jul. 22, 2003

(54) PROCESS FOR PREPARING HALOGENATED CYCLOPROPANE DERIVATIVES

(75) Inventors: Tsutomu Ebata, Tokyo (JP); Toshifumi Akiba, Tokyo (JP); Takanobu Ikeya, Tokyo (JP); Ryuhei Wakita, Osaka (JP); Mikio Sasaki, Osaka (JP)

(73) Assignees: Daiichi Pharmaceutical Co., Ltd., Tokyo (JP); Sumitomo Chemical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,054

(22) PCT Filed: Aug. 29, 1996

(86) PCT No.: PCT/JP96/02417

§ 371 (c)(1),
(2), (4) Date: Feb. 27, 1998

(87) PCT Pub. No.: WO97/08128

PCT Pub. Date: Mar. 6, 1997

(65) Prior Publication Data

US 2001/0051750 A1 Dec. 13, 2001

(30) Foreign Application Priority Data

Aug. 30, 1995 (JP) ............................... 7-221626
Jan. 24, 1996 (JP) ............................... 8-009830

(51) Int. Cl.$^7$ ..................... C07C 69/74; C07C 233/00; C07C 325/02
(52) U.S. Cl. ........................... 560/122; 564/190; 568/20
(58) Field of Search .................. 560/122; 564/190; 568/20

(56) References Cited

U.S. PATENT DOCUMENTS 5,587,386 A  12/1996  Hayakawa et al. ......... 514/312

FOREIGN PATENT DOCUMENTS

| EP | 712831 | 5/1996 | ............ C07C/61/15 |
| JP | 2-231475 | 9/1990 | ......... C07D/215/56 |
| JP | 5-139998 | 6/1993 | ............ C07B/37/10 |
| JP | 5-194323 | 8/1993 | ......... C07C/69/743 |
| JP | 6-9499 | 1/1994 | ......... C07C/69/743 |
| JP | 7-97353 | 4/1995 | ............ C07C/69/74 |

OTHER PUBLICATIONS

English Translation of JP 5–139998 by Kimura et al. published Jun. 1993, pp. 1–35.*
T. W. Graham Solomons, Oganic Chemistry, fourth edition, 1988, pp. 182 and 183.*
Callot and Metz, *Tetrahedron*, vol. 41, No. 20, pp. 4495–4501 (1985).
Demoncean, et al., *Tetrahedron*, vol. 46, No. 11, pp. 3889–3896 (1990).
Gassen et al., Journal of Fluorine Chemistry. vol. 49, pp. 127–139, 1990, XP002002458, Fluorinated Cyclopropanecarboxylic Acids and Their Derivatives.
Copy of an English Language Abstract of JP No. 2–231475.
Copy of an English Language Abstract of JP No. 6–9499.
Copy of an English Language Abstract of JP No. 5–194323.
Copy of an English Language Abstract of JP No. 7–97353.
Copy of an English Language Abstract of JP No. 5–139998.

* cited by examiner

*Primary Examiner*—Rosalynd Keys
(74) *Attorney, Agent, or Firm*—Greenblum & Bernstein, P.L.C.

(57) ABSTRACT

A process for preparing compounds represented by the following general formula (I) wherein X represents chlorine atom, bromine atom, or iodine atom, and R includes alkoxy group and amino group which comprises the step of allowing a compound represented by the formula: $CH_2=CXF$ react with a compound represented by the formula: $N_2CHCOR$ in the presence of a catalyst containing a metal atom such as a transition metal of group 8 together with chiral carboxylic-type or amide-type ligands to preferentially obtain a stereoisomer of the compound of the general formula (I) wherein the stereochemical configuration at the 1-position is S-configuration

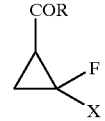

18 Claims, No Drawings

PROCESS FOR PREPARING HALOGENATED CYCLOPROPANE DERIVATIVES

This application is a 371 of PCT/JP96/02417, filed Aug. 29, 1996.

TECHNICAL FIELD

The present invention relates to a process for preparing optically active halogenated cyclopropane derivatives which are useful as synthetic intermediates for the preparation of synthetic new quinolone antibacterial agents having excellent activity and safety.

BACKGROUND ART

Among the new quinolone antibacterial agents having excellent antibacterial activity, synthetic antibacterial agents having a fluorocyclopropyl group at the 1-position of the quinolone nucleus have both excellent antibacterial activity and safety, and accordingly, they are expected as clinically useful drugs (Japanese Patent Unexamined Publication (KOKAI) No. (Hei) 2-231475/1990). Optically active 2-fluorocyclopropanecarboxylic acid and derivatives thereof having a specific stereochemical configuration, i.e., (1S, 2S), are important as synthetic intermediates for these compounds.

(1S,2S)-2-fluorocyclopropanecarboxylic acid is heretofore prepared by the steps of addition of bromofluorocarbene to butadiene to produce 1-bromo-1-fluoro-2-vinylcyclopropane; oxidation of the vinyl group to obtain a carboxylic acid and then esterification and successive debromination of the resulting product; separation of a cis-isomer from the resulting reaction mixture by distillation; hydrolysis of the ester group of the cis-isomer to afford a carboxylic acid; and optical resolution of the resulting carboxylic acid (see, the reaction scheme set out below).

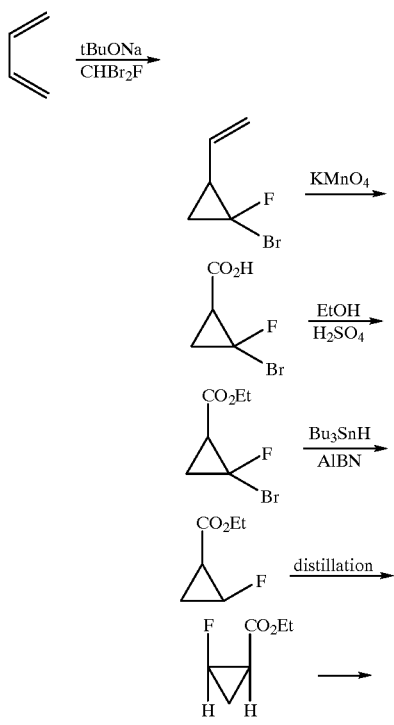

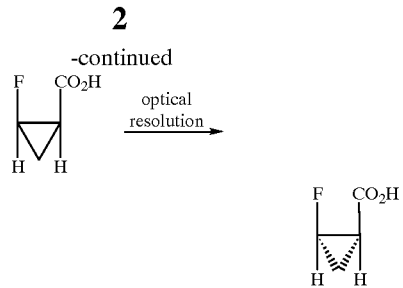

Another method for preparing (1S,2S)-2-fluorocyclopropanecarboxylic acid is known which comprises the steps of reacting a vinyl halogenide with a diazoacetic acid derivative in the presence of a variety of metal catalysts, optionally followed by additional dehalogenation reaction, separation of stereoisomers, and optical resolution (Japanese Patent Unexamined Publication (KOKAI) No. (Hei) 6-949911994 and Japanese Patent Unexamined Publication (KOKAI) No. (Hei) 5-194323/1993). However, no metal catalyst having one or more chiral ligands was used in the aforementioned processes.

These preparing processes involve the step of optical resolution of the desired optically active compound having (1S,2S)-configuration after the preparation of the racemic 1,2-cis-2-fluorocyclopropanecarboxylic acid derivative, and the (1R,2R)-isomer, which comprises the half of the racemate, have to be removed as waste matter. Therefore, these processes are not efficient from economical and industrial viewpoints.

The object of the present invention is to provide an efficient and convenient process for preparing optically active halogenated cyclopropane derivatives which are useful for the manufacture of the optically active (1S,2S)-2-fluorocyclopropane-carboxylic acid or derivatives thereof. More specifically, the object of the present invention is to provide a process for preparing the aforementioned optically active halogenated cyclopropane derivatives by a stereoselective reaction using readily available starting materials.

DISCLOSURE OF THE INVENTION

The inventors of the present invention conducted various studies to achieve the foregoing object, and as a result, they found that a 2-fluoro-2-chlorocyclopropanecarboxylic acid derivative can be obtained stereoselectively and in high yield by reacting a diazoacetic acid derivative with 1-fluoro-1-chloroethylene, for example, in the presence of a metal catalyst having one or more chiral ligands. The inventors of the present invention also found that the optically active 2-fluoro-cyclopropanecarboxylic acid derivatives having the desired stereochemical configuration, i.e., (1S,2S), can be prepared in high yield by subjecting the aforementioned 2-fluoro-2-chlorocyclopropanecarboxylic acid derivative to dehalogenation reaction. The present invention was achieved on the basis of these findings.

The present invention thus provides a process for preparing compounds represented by the following general formula (I):

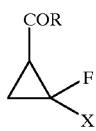

wherein:
X represents chlorine atom, bromine atom, or iodine atom;
R represents a $C_{1-10}$ (containing 1–10 carbon atoms) alkyloxy group which may have one or more halogen atoms or one or more $C_{1-10}$ alkyloxy groups;
an aralkyloxy group constituted by one or more aryl groups which may have a substituent(s) and a $C_{1-10}$ alkyloxy group;
an aryloxy group having an aryl groups which may be substituted;
  a $C_{1-10}$ alkylthio group which may have one or more halogen atoms;
an aralkylthio group constituted by an aryl group which may have a substituent(s) and a $C_{1-10}$ alkylthio group;
amino group; or
a substituted amino group which has one or more substituents selected from the group consisting of a $C_{1-10}$ alkyl group, an aryl group which may be substituted, an aralkyl group constituted by an aryl group which may have a substituent(s) and a $C_{1-10}$ alkyl group, and an acyl group; provided that substituents of the substituted aryl groups are selected from the group consisting of a halogen atom, a $C_{1-10}$ alkyl group, a $C_{1-10}$ halogenoalkyl group, a $C_{1-10}$ alkyloxy group, a carbamoyl group which may be substituted, hydroxyl group, nitro group, cyano group, and an amino group which may be substituted,
characterized in that the process comprises the step of allowing a compound represented by the formula: $N_2CHCOR$ wherein R is the same as that defined above react with a compound represented by the formula: $CH_2=CXF$ wherein X is the same as that defined above in the presence of a catalyst comprising a metal atom selected from the group consisting of a transition metal of group 8, molybdenum, and copper, together with at least one chiral ligand selected from the group consisting of a carboxylic acid-type ligand, an amide-type ligand, a phosphine-type ligand, an oxime-type ligand, a sulfonic acid-type ligand, 1,3-diketone-type ligand, a Schiff base-type ligand, an oxazoline-type ligand, and a diamine-type ligand to preferentially produce a stereoisomer of the compound of the general formula (I) wherein the stereochemical configuration at the I-position is S-configuration.

According to preferred embodiments of the above invention, there are provided the aforementioned process which preferentially produces a stereoisomer of a compound of the general formula (I) wherein the stereochemical configuration at the 1-position is S-configuration and the substituent represented by —COR and the fluorine atom is in cis-configuration; the aforementioned process which preferentially produces a stereoisomer of the compound of the general formula (I) wherein the stereochemical configuration at the 1-position is S-configuration and the substituent represented by —COR and the fluorine atom is in trans-configuration; the aforementioned process wherein X is chlorine atom or bromine atom; the aforementioned process wherein R is a $C_{1-10}$ alkyloxy group; the aforementioned process wherein R is a $C_{1-6}$ alkyloxy group; and the aforementioned process wherein R is ethoxy group.

As preferred embodiments of the aforementioned invention, there are also provided the aforementioned process which is carried out in the presence of said catalyst containing at least one chiral ligand selected from the group consisting of a carboxylic acid-type ligand and an amide-type ligand; the aforementioned process which is carried out in the presence of a catalyst containing at least one chiral ligand selected from the group consisting of a carboxylic acid-type ligand and an amide-type ligand together with at least one ligand selected from the group consisting of a halogen-type ligand, a phosphine-type ligand, an oxime-type ligand, a sulfonic acid-type ligand, a 1,3-diketone-type ligand, a Schiff base-type ligand, and a carbon monoxide type ligand; the aforementioned process which is carried out in the presence of a catalyst containing at least one chiral ligand selected from the group consisting of a carboxylic acid-type ligand and an amide-type ligand together with at least one ligand selected from the group consisting of a halogen-type ligand, a phosphine-type ligand, and a carbon monoxide type ligand; and the aforementioned process which is carried out in the presence of said catalyst containing at least one chiral ligand selected from the group consisting of an oxazoline-type ligand and a diamine-type ligand.

As preferred embodiments of the aforementioned invention, there are further provided the aforementioned process which is carried out in the presence of the catalyst containing two or more identical chiral ligands selected from the group consisting of a carboxylic acid-type ligand and an amide-type ligand; the aforementioned process which is carried out in the presence of the catalyst containing the identical chiral ligands selected from the group consisting of a carboxylic acid-type ligand and an amide-type ligand; the aforementioned process which is carried out in the presence of the catalyst containing at least one carboxylic acid-type chiral ligand; the aforementioned process which is carried out in the presence of the catalyst containing two or more identical carboxylic acid-type chiral ligands; the aforementioned process which is carried out in the presence of the catalyst containing as ligands only identical carboxylic acid-type optically active ligands; the aforementioned process which is carried out in the presence of the catalyst containing at least one amide-type chiral ligand; the aforementioned process which is carried out in the presence of the catalyst containing two or more identical amide-type chiral ligands; the aforementioned process which is carried out in the presence of the catalyst containing as ligands only identical amide-type chiral ligands; the aforementioned process which is carried out in the presence of said catalyst containing cobalt, rhodium, iridium, ruthenium, palladium, molybdenum, copper, or iron as the metal atom; and the aforementioned process which is carried out in the presence of said catalyst containing rhodium as the metal atom. As preferred embodiments of the aforementioned invention, there are also provided the aforementioned process which is carried out in the presence of the catalyst containing at least one chiral ligand selected from the group consisting of an oxazoline-type ligand and a diamine-type ligand; the aforementioned process which is carried out in the presence of the catalyst containing copper as the metal atom; and the aforementioned process wherein a copper source is at least one substance selected from the group consisting of copper (I) trifluoromethanesulfonate $[CuOSO_2CF_3]$ and copper (II) trifluoromethanesulfonate $[Cu(OSO_2CF_3)_2]$.

BEST MODE FOR CARRYING OUT THE INVENTION

The first embodiment of the process of the present invention is characterized in that, where a compound of the general formula (II) represented by $CH_2=CXF$ and a compound of the general formula (III) represented by $N_2CHCOR$ are reacted to give a compound of the general formula (I), the process is carried out in the presence of the aforementioned specific catalyst to preferentially produce a stereoisomer of the compound of the general formula (I) wherein the stereochemical configuration at the 1-position is S-configuration (in the specification, among the carbon atoms constituting the cyclopropane ring, the carbon atom to which the substituent —COR binds is referred to as the carbon atom at the 1-position).

One embodiment of the present invention is characterized in that a stereoisomer of the compound of the general formula (I) is preferentially formed wherein the stereochemical configuration at the 1-position is S-configuration and the substituent represented by —COR and the fluorine atom are in cis-configuration (the term "cis-configuration" herein used means that the substituent represented by —COR and the fluorine atom on the cyclopropane ring are present on the same side of the plane provided by the cyclopropane ring). Another embodiment of the present invention is characterized in that a stereoisomer of the compound of the general formula (I) is preferentially formed wherein the stereochemical configuration at the 1-position is S-configuration and the substituent represented by —COR and the fluorine atom are in trans-configuration.

In each of the inventions mentioned above, the wording "a stereoisomer is preferentially formed" means that the produced amount of the desired stereoisomer as the target among the compounds of formula (I) exceeds those of the other stereoisomers. In the specification, this wording should be construed in its broadest meaning, which includes where the produced amount of the desired stereoisomer only slightly exceeds those of the other stereoisomers, and where only the desired stereoisomer is substantially produced, but excludes where the produced amount of the desired stereoisomer is completely the same as those of the other stereoisomer.

In the compounds represented by the general formula (I) and the general formula (II), X represents chlorine atom, bromine atom, or iodine atom. Among them, X may preferably be chlorine atom or bromine atom. As the compound of the above general formula (I), 2-chloro-2-fluorocyclopropanecarboxylic acid derivatives and 2-bromo-2-fluorocyclo-propanecarboxylic acid derivatives are preferred.

In the compounds of the general formula (I) and the general formula (III), R represents a $C_{1-10}$ alkyloxy group (preferably a $C_{1-6}$ alkyloxy group) which may have one or more halogen atoms or one or more $C_{1-10}$ alkyloxy groups (preferably a $C_{1-6}$ alkyloxy group);
an aralkyloxy group constituted by an aryl group which may be substituted and a $C_{1-10}$ alkyloxy group (preferably a $C_{1-6}$ alkyloxy group);
an aryloxy group having one or more aryl groups which may be substituted;
a $C_{1-10}$ alkylthio group (preferably a $C_{1-6}$ alkylthio group) which may have one or more halogen atoms;
an aralkylthio group constituted by an aryl group which may have a substituent(s) and a $C_{1-10}$ alkylthio group (preferably a $C_{1-6}$ alkylthio group);
amino group; or
a substituted amino group which has one or two substituents selected from the group consisting of a $C_{1-10}$ alkyl group (preferably a $C_{1-6}$ alkyl group), an aryl group which may be substituted, an aralkyl group constituted by an aryl group which may be substituted together with a $C_{1-10}$ alkyl group (preferably a $C_{1-6}$ alkyl group), and an acyl group.

In the above definition, substituents of the substituted aryl groups are selected from the group consisting of a halogen atom, a $C_{1-10}$ alkyl group (preferably a $C_{1-6}$ alkyl group), a $C_{1-10}$ halogenoalkyl group (preferably a $C_{1-6}$ halogenoalkyl group), a $C_{1-10}$ alkyloxy group (preferably a $C_{1-6}$ alkyloxy group), a carbamoyl group which may be substituted, hydroxyl group, nitro group, cyano group, and an amino group which may be substituted.

In the above definition of R, the alkyloxy group may be a straight chain-, a branched chain-, or a cyclic alkyl. As the $C_{1-10}$ alkyloxy group, for example, methoxy group, ethoxy group, n-propoxy group, isopropoxy group, cyclopropoxy group, n-butoxy group, sec-butoxy group, tert-butoxy group, cyclobutoxy group, n-pentoxy group, n-hexoxy group, cyclohexyloxy group, levo-menthyloxy group or the like can be used. These $C_{1-10}$ alkyloxy groups may be substituted with one or more halogen atoms (when the term "halogen atom" is herein referred to, the term is used so as to include any of fluorine atom, chlorine atom, bromine atom, and iodine atom unless specifically indicated), or with one or more $C_{1-10}$ alkyloxy groups (for example, those exemplified above, preferably $C_{1-6}$ alkyloxy groups). As the alkyloxy group represented by R, a straight chain- or branched chain-$C_{1-6}$ alkyloxy group is preferred, and ethoxy group or methoxy group is particularly preferred.

The aralkyloxy group is constituted by an aryl group such as phenyl group and naphthyl group (which may be substituted) together with the $C_{1-10}$ alkyloxy group mentioned above. Examples of the aralkyloxy group include, for example, benzyloxy group, diphenylmethyloxy group, and triphenylmethyloxy group. When the aralkyloxy group has two or more aryl groups, those aryl groups may be identical or different. The aryl group constituting the aryloxy group may be any one of aryl groups which may be substituted. For example, phenyl group or naphthyl group may suitably used. Examples of the aryloxy group include, for example, phenoxy group, 1-naphthoxy group, and 2-naphthoxy group.

The $C_{1-10}$ alkylthio group and aralkylthio group correspond to the $C_{1-10}$ alkyloxy group and aralkyloxy group explained above, respectively, in which the oxygen atom constituting the oxy group is replaced with a sulfur atom.

When R represents a substituted amino group, examples of a usable substituent on the amino group include a $C_{1-10}$ alkyl group, an aryl group which may be substituted, an aralkyl group constituted by an aryl group which may be substituted together with a $C_{1-10}$ alkyl group, and an acyl group. When two substituents bind to the amino group, they may be the same or different.

With regard to the substituents on the amino group mentioned above, the $C_{1-10}$ alkyl group may be any one of straight chain-, branched chain-, or cyclic alkyl. For example, methyl group, ethyl group, n-propyl group, isopropyl group, cyclopropyl group, n-butyl group, sec-butyl group, tert-butyl group, cyclobutyl group, n-pentyl group, n-hexyl group, cyclohexyl group, or 1-menthyl group may be used. As the aryl group, phenyl group, naphthyl group, and the like can be used. The aralkyl group is constituted by an aryl group such as phenyl group or naphthyl group (which may be substituted) together with the aforementioned $C_{1-10}$ alkyl group. For example, benzyl group, diphenylmethyl group, triphenylmethyl group can be used. As the acyl group, either of an aliphatic acyl group constituted by the aforementioned $C_{1-10}$ alkyl group together with carbonyl group, or an aromatic acyl group constituted by an aryl group which may be substituted together with carbonyl group can be used. For example, acetyl group, benzoyl group and the like can be used.

With regard to the substituent explained above, a substituent selected from the group consisting of a halogen atom, the aforementioned $C_{1-10}$ alkyl group, a $C_{1-10}$ halogenoalkyl group being a $C_{1-10}$ alkyl group substituted with one or more halogen atoms, the aforementioned $C_{1-10}$ alkyloxy group, a carbamoyl group which may be substituted, hydroxyl group, nitro group, cyano group, and an amino group which may be substituted can be used as the substituent of the substituted aryl group. When the aryl group has two or more substituents, those substituents may be the same or different. When a substituted amino group and/or a substituted carbamoyl group is used as one or more substituents on the aryl group, the substituents on the amino group, those explained above as to the definition wherein R is a substituted amino group, may be used as substituents on the amino group and/or the carbamoyl group.

The process of the present invention is characterized in that the process utilizes a catalyst containing a metal atom selected from the group consisting of a transition metal of group 8, molybdenum, and copper, together with at least one chiral ligand selected from the group consisting of a carboxylic acid-type ligand, an amide-type ligand, a phosphine-type ligand, an oxime-type ligand, a sulfonic acid-type ligand, a 1,3-diketone-type ligand, a Schiff base-type ligand, an oxazoline-type ligand, and a diamine type ligand for the reaction of a compound of the formula (II) and a compound of the formula (III). As to the ligand of the catalyst, the ligand is specified in the specification based on the type of a functional group coordinating to the metal atom of the catalyst. For example, when carboxyl group in a ligand coordinates to a metal atom, the ligand is referred to as a carboxylic acid-type ligand. However, where a carboxylic acid ligand, for example, is referred to in the specification, one or more functional groups other than carboxyl group (e.g., one or more functional groups such as an alkyl group, an aryl group, an aralkyl group, and a heterocyclic group) may be present in the ligand. As to an amide-type ligand, a phosphine-type ligand, an oxime-type ligand, a sulfonic acid-type ligand, a 1,3-diketone-type ligand, a Schiff base-type ligand, an oxazoline-type ligand, and a diamine-type ligand, the wording should be interpreted similarly.

Among the catalysts comprising the aforementioned components, for example, the following catalysts are preferably used for the process of the present invention:

(a) the aforementioned catalyst which contains at least one chiral ligand which is selected from the group consisting of a carboxylic acid-type ligand and an amide-type ligand;

(b) the catalyst which contains at least one chiral ligand selected from the group consisting of a carboxylic acid-type ligand and an amide-type ligand, together with at least one ligand which is selected from the group consisting of a halogen-type ligand, a phosphine-type ligand, an oxime-type ligand, a sulfonic acid-type ligand, a 1,3-diketone-type ligand, a Schiff base-type ligand, and a carbon monoxide-type ligand;

(c) the catalyst which contains at least one chiral ligand which is selected from the group consisting of a carboxylic acid-type ligand and an amide-type ligand, together with at least one ligand selected from the group consisting of a halogen-type ligand, a phosphine-type ligand, and a carbon monoxide-type ligand;

(d) the catalyst which contains at least one chiral ligand which is selected from the group consisting of an oxazoline-type ligand and a diamine-type ligand; and the like.

Iron, nickel, rhodium, palladium, cobalt, iridium, ruthenium, and the like may preferably be used as the transition metal of group 8, and as a metal other than the transition metals of group 8, molybdenum or copper can be used. It is preferred that the valence of these metal atoms are divalent at forming the catalyst. Where a metal such as copper is used, the metal may be monovalent. Examples of preferred metal atoms include, for example, rhodium, palladium, cobalt, iridium, ruthenium, molybdenum, copper, and iron.

The catalyst used for the process of the present invention is characterized in that it contains at least one chiral ligand. The chiral ligand is selected from the group consisting of a carboxylic acid-type ligand, an amide-type ligand, a phosphine-type ligand, an oxime-type ligand, a sulfonic acid-type ligand, a 1,3-diketone-type ligand, a Schiff base-type ligand, an oxazoline-type ligand, and a diamine-type ligand, and preferably, the ligand is selected from the group consisting of a carboxylic acid-type ligand, an amide-type ligand, an oxazoline-type ligand, and a diamine-type ligand. When two or more chiral ligands coordinate to the aforementioned metal, it is preferable that each of the chiral ligands is structurally and optically identical. However, two or more different types of optically active ligands may coordinate to the metal.

For example, all of the ligands on the aforementioned metal may be chiral ligands selected from a carboxylic acid-type ligand and an amide-type ligand. Alternatively, for example, one or more chiral ligands among the ligands on the metal may be selected from the group consisting of a carboxylic acid-type ligand and an amide-type ligand, and the other one or more ligands may be selected from the group consisting of a halogen-type ligand, a phosphine-type ligand, an oxime-type ligand, a sulfonic acid-type ligand, a 1,3-diketone-type ligand, a Schiff base-type ligand, and a carbon monoxide-type ligand, preferably from the group consisting of a halogen-type ligand, a phosphine-type ligand, and a carbon monoxide-type ligand. In this case, the aforementioned ligands other than the carboxylic acid and the amide types may be chiral ligands.

As a compound for providing the chiral carboxylic acid-type ligand, for example, optically active amino acids or optically active carboxylic acids having one or more asymmetric carbons can be used. As the optically active amino acids, for example, D- or L-alanine, arginine, asparagine, aspartic acid, cysteine, cystine, histidine, hydroxylysine, hydroxyproline, isoleucine, leucine, lysine, methionine, phenylalanine, proline, serine, threonine, thyroxine, tryptophane, tyrosine, valine, aminobutyric acid, citrulline, cystathionine, phenylglycine, methionine, norleucine, norvaline, glutamic acid, glutamine, penicillamine, pipecolic acid, 3,5-dibromotyrosine, 3,5-diiodotyrosine and other may be used.

As the optically active carboxylic acids, for example, 2-chloropropionic acid, 2-bromopropionic acid, 2-acetoxypropionic acid, 2,3-diaminopropionic acid, 2-phenylpropionic acid, 2-chloro-3-phenylpropionic acid, 2-hydroxy-3-phenylpropionic acid, 2-(6-methoxy-2-naphthyl)propionic acid, 3-acetylthio-2-methylpropionic acid, 2-amino-3-guanidinopropionic acid, 3-acetylthioisobutyric acid, 2-chlorobutyric acid, 2-chloro-3-methylbutyric acid, 3-hydroxybutyric acid, 2,4-diaminobutyric acid, 2-methylbutyric acid, 2-phenylbutyric acid, 3-phenylbutyric acid, 2-chloro-3-methylvaleric acid, 2-chloro-4-methylvaleric acid, menthoxyacetic acid, 2-methoxyphenylacetic acid, 2-methoxy-2-trifluoromethylphenylacetic acid, phenylsuccinic acid, shikimic acid, camphoric acid, mandelic acid, hexahydromandelic acid, monomenthyl phthalate, N-(α-methylbenzyl)

phthalic acid monoamide, 2-oxothiazolidine-4-carboxylic acid, 3-phenyllactic acid, lactic acid, 4-hydroxypyrroline, pyroglutamic acid, malic acid, 2-methylmalic acid, 2-benzamidecyclohexanecarboxylic acid, 3-methyladipic acid, tartaric acid and other may be used.

Among functional groups existing in the chiral amino acids or the chiral carboxylic acids mentioned above, functional groups other than the carboxyl group for coordinating to the metal atom (e.g., amino group) may be protected by means of a protective group available to those skilled in the art. As protective groups for amino group, for example, maleic anhydride, 2,3-dichloromaleic anhydride, phthalic anhydride, 3,6-dichlorophthalic anhydride, 4,5-dichlorophthalic anhydride, 3,6-difluorophthalic anhydride, 4,5-difluorophthalic anhydride, 3,4,5,6-tetrachlorophthalic anhydride, 3,4,5,6-tetrafluorophthalic anhydride, hexahydrophthalic anhydride, 1,2,3,6-tetrahydrophthalic anhydride, glutaric anhydride, 3-methylglutaric anhydride, itaconic anhydride, 1,8-naphthalic anhydride, succinic anhydride, tetrafluorosuccinic anhydride, 3,4,5,6-tetrahydrosuccinic anhydride, citraconic anhydride, 1-cyclopentene-1,2-dicarboxylic anhydride, cis-endo-5-norbornene-2,3-dicarboxylic anhydride, bicyclo[2.2.1]hept-5-ene-2,3-dicarboxylic anhydride, formyl group, acetyl group, benzoyl group, trifluoroacetyl group, benzyloxycarbonyl group, methoxycarbonyl group, tert-butoxycarbonyl group, trifluoromethanesulfonyl group, p-toluenesulfonyl group and other may be used.

As a compound for providing the optically active amide-type ligand, examples include 3-acetamidopyrrolidine, 1-benzoyl-2-tert-butyl-3-methyl-4-imidazolidinone, 1-tert-butoxycarbonyl-2-tert-butyl-3-methyl-4-imidazolidinone, 4-amino-3-isoxazolidone, 1,5-dimethyl-4-phenyl-2-imidazolidinone, N-(3,5-dinitrobenzoyl)-1-phenylethylamine, 5-(hydroxymethyl)-2-pyrrolidinone, 4-isopropyl-2-oxazolizinone, 4-methyl-5-phenyl-2-oxazolizinone, 2-oxothiazolidine-4-carboxylic acid, 4-phenyloxazolidin-2-one, prolineamide, proline-2-naphthylamide, pyroglutamic acid ethyl ester, pyroglutamic acid 2-naphthylamide and other.

As a compound for providing the chiral oxazoline-type ligand, for example, an example includes the compounds set out below:

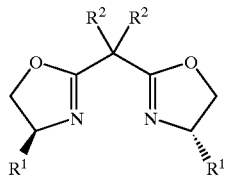

wherein $R^1$ represents a lower alkyl group having 1 to 5 carbon atoms or a phenyl group which may be substituted, and $R^2$ represents hydrogen atom or methyl group.

As specific compounds for providing the chiral oxazoline-type ligand, examples include, compounds wherein the stereochemistry of each of the asymmetric carbon atoms bound by $R^1$ is S-configuration, including 2,2'-methylenebis[(4S)-4-tert-butyl-2-oxazoline], 2,2'-isopropylidene-bis-[(4S)-4-tert-butyl-2-oxazoline], 2,2'-methylenebis[(4S)-4-isopropyl-2-oxazoline], 2,2'-isopropylidenebis[(4S)-4-isopropyl-2-oxazoline], 2,2'-isopropylidenebis[(4S)-4-benzyl-2-oxazoline] and other.

As a compound for providing the chiral diamine-type ligand, an example includes the compounds set out below:

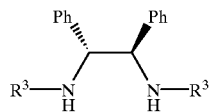

wherein $R^3$ represents benzyl group, 2,4,6-trimethylphenylmethyl group, or diphenyl-methyl group.

As specific compounds for providing the chiral diamine-type ligand, examples include, compounds wherein the stereochemistry of each of the asymmetric carbon atoms bound by the phenyl group is R-configuration, including (1R,2R)-1,2-diphenyl-N,N'-bis[2,4,6-trimethylphenylmethyl]-ethylenediamine, (1R,2R)-1,2-diphenyl-N,N'-bisbenzylethylenediamine and other.

The halogen type-ligand, the phosphine-type ligand, the oxime-type ligand, the sulfonic acid-type ligand, the 1,3-diketone-type ligand, the Schiff basetype ligand, and the carbon monoxide-type ligand are well-known to those skilled in the art and can be appropriately chosen.

As examples of the catalyst preferably used for the process of the present invention, catalysts comprising divalent rhodium together with chiral carboxylic acid-type ligands are shown below. However, the catalysts used for the process of the present invention are not limited to those indicated below.

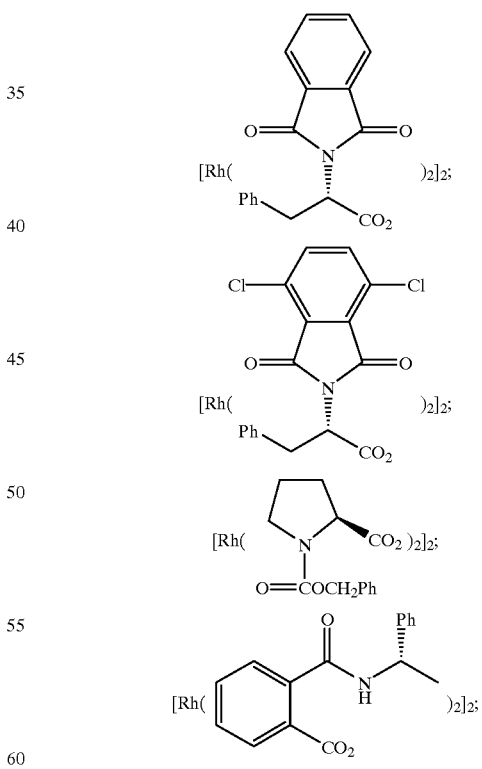

As other examples of the catalyst preferably used for the process of the present invention, catalysts having chiral amide-type ligands are shown below. However, the catalysts used for the process of the present invention are not limited to those set out below.

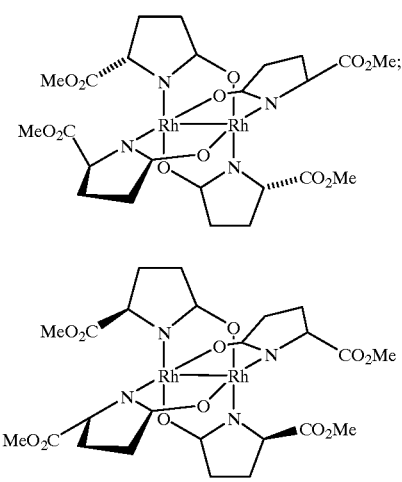

Those catalysts mentioned above can be prepared by, for example, a method comprising the steps of adding rhodium (II) acetate dimer and an excess amount of a carboxylic acid or an amide compound to chlorobenzene, and refluxing the mixture and then purifying the product (Callot, H. J. and Mets, F., Tetrahedron, 41, 4495, 1985). They can also be produced by refluxing a mixture of rhodium (II) chloride trihydrate, carboxylic acid compound, and sodium hydrogencarbonate in anhydrous ethanol under inert atmosphere, and then purifying the product (Demoncean, A., et al., Tetrahedron, 46, 3889, 1990). However, the catalysts used for the process of the present invention are not limited to those produced by the aforementioned preparing methods. It can be readily understood that the aforementioned catalysts can also be appropriately prepared by suitably altering or modifying the reaction conditions, reagents or other specified for the methods disclosed in the literatures.

Among the catalysts suitably used for the present invention, examples of catalysts containing one or more oxazoline-type ligands or diamine-type ligands together with copper include, for example, a catalyst obtainable from 2,2'-isopropylidenebis[(4S)-4-tert-butyl-2-oxazoline] and copper (I) trifluoromethane-sulfonate; a catalyst obtainable from 2,2'-isopropylidenebis[(4S)-4-tert-butyl-2-oxazoline] and copper (II) trifluoromethane-sulfonate; a catalyst obtainable from 2,2'-isopropylidenebis[(4S)-4-tert-butyl-2-oxazoline], copper (II) trifluoromethanesulfonate and phenylhydrazine; a catalyst obtainable from 2,2'-methylenebis[(4S)-4-tert-butyl-2-oxazoline] and copper (II) trifluoromethanesulfonate; a catalyst obtainable from (1R, 2R)-1,2-diphenyl-N,N'-bis[2,4,6-trimethylphenylmethyl]-ethylenediamine, copper (II) trifluoromethanesulfonate and phenylhydrazine and other. However, the catalysts used for the process of the present invention are not limited to those mentioned above.

For example, the process of the present invention can be carried out as explained below. The diazoacetic acid derivatives represented by the formula (III) can be prepared by a method well-known to those skilled in the art. For example, a diazoacetic acid ester and diazoacetic acid amide can be easily produced by subjecting respective corresponding compounds having an amino group to diazotization reaction. The 1-fluoro-1-haloethylenes represented by the formula (II) are generally of a lower boiling point, and they can be used after liquefaction at a low temperature or dissolution in an organic solvent. They can also be used under elevated pressure as required. For the reaction, examples of an applicable process include a process comprising the steps of adding a necessary amount of the aforementioned catalyst to an ethylene compound of the formula (II) or its solution, and then adding a compound of the formula (III) to the mixture; or a process comprising the steps of adding a compound of the formula (III) to an ethylene compound of the formula (II) or its solution, and then adding a necessary amount of the aforementioned catalyst to the mixture.

The above reaction can be carried out in the presence or absence of a solvent. When a solvent is used, types of the solvent are not limited so long as they, per se, are inert in the reaction. For example, aprotic solvents can be used, and preferably, aliphatic hydrocarbons, halogenated hydrocarbons, ethers and other can be used. More specifically, aliphatic hydrocarbons such as n-hexane, n-heptane, and cyclohexane; halogenated hydrocarbons such as dichloromethane and 1,2-dichloroethane; and ethers such as diethyl ether and tetrahydrofuran can be used. Among them, dichloromethane, n-heptane, or cyclohexane is most generally used.

Amount of the catalyst is not particularly limited. In general, the amount can be suitably chosen within a range of a so-called catalytic amount. For example, the aforementioned catalyst can be used in a molar amount of about 10% or less based on the molar amount of the compound of the general formula (III), preferably in a molar amount within a range of around 0.01–10%. The reaction may be carried out under cooling, at room temperature, or under warming. For example, the reaction may be carried out at a temperature in a range of from about −100° C. to 100° C., preferably from about −50° C. to 50° C. Reaction time may generally be in a range of from about 30 minutes to about 48 hours, usually in a range of from about 1 hour to 24 hours. The reaction may be carried out under elevated pressure by using a sealed vessel such as an autoclave.

According to the aforementioned process of the present invention, either a stereoisomer wherein the stereochemical configuration at the 1-position is S-configuration and the substituent represented by —COR and the fluorine atom are in cis-configuration, or a stereoisomer wherein the stereochemical configuration at the 1-position is S-configuration and the substituent represented by —COR and the fluorine atom are in trans-configuration can be preferentially prepared by suitably choosing the type of the catalyst used or other conditions. Those skilled in the art will readily understand that they can appropriately choose such catalyst by referring to the present specification.

A stereoisomer of a compound of the general formula (I) produced according to the aforementioned process of the present invention can be readily converted into a 2-fluorocyclopropanecarboxylic acid derivative by subjecting the stereoisomer to dehalogenation reaction (as to this reaction, fluorine atom is excluded from "halogen") to replace the substituent X with hydrogen atom. Therefore, according to further embodiments of the present invention, there are provided a process for preparing (1S,2S)-2-fluorocyclopropanecarboxylic acid derivatives which comprises the steps of preparing a stereoisomer of the compound of the general formula (I) according to the aforementioned process; and then subjecting the resulting stereoisomer to dehalogenation to prepare a (1S,2S)-2-fluorocyclopropanecarboxylic acid derivative; and a process for preparing (1S,2S)-2-fluorocyclopropanecarboxylic acid derivatives which comprises the step of subjecting a stereoisomer of the compound of the general formula (I) prepared according to the aforementioned reaction to dehalogenation reaction without isolation or purification.

When the stereoisomer wherein the stereochemical configuration at the 1-position is S-configuration and the substituent represented by —COR and the fluorine atom is in cis-configuration is produced according to the process of the present invention, (1S,2S)-2-fluorocyclopropanecarboxylic acid can be prepared by carrying out a retention reaction as the dehalogenation reaction. On the other hand, when the stereoisomer wherein the stereochemical configuration at the 1-position is S-configuration and the substituent represented by —COR and the fluorine atom is in trans-configuration is produced according to the process of the present invention, (1S,2S)-2-fluorocyclopropanecarboxylic acid can be prepared by carrying out an inversion reaction as the dehalogenation reaction.

Methods for the dehalogenation are not particularly limited. For example, hydrogenolysis by using Raney nickel catalyst in the presence of hydrogen gas flow and a base is preferable (Japanese Patent Unexamined Publication (KOKAI) No. (Hei) 7-97353/1995). This dehalogenation proceeds as retention of configuration, and accordingly, it is preferred to employ this dehalogenation when the stereoisomer of the compound of the general formula (I) wherein the stereochemical configuration at the 1-position is S-configuration and the substituent represented by —COR and the fluorine atom is in cis-configuration is produced according to the process of the present invention.

Optical purity of the resulting 2-fluoro- cyclopropanecarboxylic acid derivative can be readily determined by means of, for example, a gas chromatographic analysis using an optically active capillary column after the 2-fluorocyclopropanecarboxylic acid derivative is converted into an ester compound. Alternatively, a liquid chromatographic analysis may also be applicable after the 2-fluorocyclopropanecarboxylic acid derivative is converted into an optically active amide compound such as a 1-phenylethylamide derivative.

EXAMPLES

The present invention will be explained more specifically by referring to the following examples. However, the scope of the present invention is not limited to these examples.

Example 1

(1S,2S)-2-Fluorocyclopropanecarboxylic Acid Ethyl Ester

Dichloromethane (10 ml) was charged in a two-neck flask and cooled to about −60° C., and then was bubbled 1-chloro-1-fluoroethylene till 4.5 g of the gas was dissolved. This solution was added with dirhodium (II) tetrakis(N-(3,6-dichlorophthaloyl)-L-phenylalanine) (84 mg), and then the reaction mixture was cooled to be kept at −40° C. Ethyl diazoacetate (corresponding to 5 mmol) was dissolved in dichloromethane, and then the resulting solution was cooled with dry ice/acetone and added dropwise to the aforementioned reaction mixture over 30 minutes. After the dropwise addition was completed, the reaction mixture was analyzed by gas chromatography to find that 2-chloro-2-fluorocyclopropanecarboxylic acid ethyl ester was formed in a 86% yield and the produced ratio of the cis-isomer and the trans-isomer was 1.46:1.

Physicochemical properties of these products were as follows:
$^1$H-NMR 400 MHz (CDCl$_3$) δppm:
Cis-isomer: 1.30 (3H, t, J=7.3 Hz), 1.69 (1H, td, J=7.3, 9.3Hz), 2.24 (1H, td, J=7.8, 16.1 Hz), 2.38 (1H, ddd, J=1.0, 7.8, 10.0 Hz), 4.22 (2H, q, J=7.3 Hz)
Trans-isomer: 1.31 (3H, t, J=7.3 Hz), 1.83–1.94 (2H, m), 2.54(1H, m), 4.23 (2H, q, J=7.3 Hz)
Retention times observed by gas chromatographic analysis [column: TC-WAX (GLSciences) 30 m×0.25 mm ø, column temperature: 70° C., injector temperature: 200° C., detector temperature: 200° C., carrier gas: helium]:
Cis-isomer: 6.7 minutes
Trans-isomer: 6.2 minutes The resulting ethyl 2-chloro-2-fluoro- cyclopropanecarboxylate was charged into an autoclave, and added with Raney nickel (0.5 ml) and ethanol (5 ml). The mixture was further added with 1,2-diaminoethane (0.54 g) and stirred at room temperature under hydrogen atmosphere at 50 Kgf/cm$^2$ for 24 hours. After the completion of the reaction, Raney nickel was removed by filtration, and then the resulting reaction mixture was analyzed by gas chromatography to find that ethyl 2-fluorocyclopropanecarboxylate was formed quantitatively and the optical purity of ethyl (1S,2S)-2-fluorocyclopropanecarboxylate was 21% e.e.

Analytical data of the products were as follows:
$^1$H-NMR 400 MHz (CDCl$_{13}$) δppm:
Cis-isomer: 1.11–1.18 (1H, m), 1.29 (3H, t, J=7.1 Hz), 1.75–1.84 (2H, m), 4.20 (2H, q, J=7.1 Hz), 4.73 (1H, dm, J=65.1 Hz)
Trans-isomer: 1.24–1.34 (1H, m), 1.27 (3H, t, J=7.1 Hz), 1.41–1.49 (1H, m), 2.04–2.11 (1H, m), 4.14 (2H, q, J=7.1 Hz), 4.80 (1H, dm, J=63.5 Hz)
Retention times observed by gas chromatographic analysis [column: CP-Cyclodex-β-236M 25 m×0.25 mm ø, column temperature: 75° C., injector temperature: 200° C., detector temperature: 200° C., carrier gas: helium]:
Ethyl (1S,2S)-2-fluorocyclopropanecarboxylate: 9.8 minutes
Ethyl (1R,2R)-2-fluorocyclopropanecarboxylate: 9.4 minutes Example 2

(1S,2S)-2-Fluorocyclopropanecarboxylic Acid Ethyl Ester

In a similar manner to that of Example 1, tetrakis(N-benzyloxycarbonyl-L-proline) dirhodium (II) (30 mg) was added to a solution of 1-chloro-1-fluoroethylene (3.7 g) in dichloromethane (5 ml). A chilled solution of dichloromethane containing ethyl diazoacetate (corresponding to 2.5 mmol) was added dropwise to the solution over about 30 minutes. After the completion of the dropwise addition, the reaction mixture was analyzed by gas chromatography to find that ethyl 2-chloro-2-fluorocyclopropanecarboxylate was formed in a 73% yield and the produced ratio of the cis-isomer and the trans-isomer was 1.39:1. The resulting ethyl 2-chloro-2-fluorocyclopropanecarboxylate was converted into ethyl 2-fluorocyclopropanecarboxylate in a similar manner to that of Example 1. The conversion ratio of the reaction was found to be 100%, and the optical purity of ethyl (1S,2S)-2-fluorocyclopropanecarboxylate was 19% e.e.

Example 3

(1S,2S)-2-Fluorocyclopropanecarboxylic Acid Ethyl Ester

In a similar manner to that of Example 1, tetrakis[(−)-cis-2-benzamidecyclohexanecarboxylate] dirhodium (II) (60 mg) was added to a solution of 1-chloro-1-fluoroethylene (7.7 g) in dichloromethane (10 ml). A chilled dichloromethane solution containing ethyl diazoacetate (corresponding to 5 mmol) was added dropwise to the solution over about 30 minutes. After the dropwise addition was completed, the reaction mixture was analyzed by gas chromatography to find that ethyl 2-chloro-2-fluorocyclopropanecarboxylate was formed in a 71% yield and the produced ratio of the cis-isomer and the trans-isomer was 1.25:1. The resulting ethyl 2-chloro-2-fluorocyclopropanecarboxylate was converted into ethyl 2-fluorocyclopropane-carboxylate in a similar manner to that of Example 1. The conversion ratio of the reaction was found to be 100%, and the optical purity of ethyl (1S,2S)-2-fluorocyclopropanecarboxylate was 18% e.e.

Example 4

Ethyl 2-chloro-2-fluorocyclopropanecarboxylate

Cyclohexane (76.6 g), 2,2'-isopropylidenebis[(4S)-4-tert-butyl-2-oxazoline] (64.8 mg, 0.22 mmol), and copper (II) trifluoromethanesulfonate (72.1 mg, 0.20 mmol) were charged in an autoclave, and then 1-chloro-1-fluoroethylene (76.8 g, 0.95 mol) was charged under elevated pressure. After the mixed solution was cooled to 10° C., a mixed solution containing 95% of ethyl diazoacetate (12.0 g, 100 mmol) and cyclohexane (50 g) was charged under elevated pressure over five hours. Cyclohexane (20 ml) was further charged under elevated pressure and stirring was continued at the same temperature for 1 hour, and then the internal pressure was released to give a solution of ethyl 2-chloro-2-fluorocyclopropanecarboxylate in cyclohexane (179.3 g). This solution was analyzed by gas chromatography to find that the content of the ethyl 2-chloro-2-fluorocyclopropanecarboxylate was 6.52% (yield based on ethyl diazoacetate: 70.1%), and the ratio of cis-isomer/trans-isomer was 64.4/35.6.

After the cyclohexane was evaporated under reduced pressure from a part of the resulting reaction mixture, ethyl 2-chloro-2-fluorocyclopropanecarboxylate was obtained by distillation under reduced pressure at 20 mmHg. The product was analyzed by gas chromatography to find that the optical purity of the cis-isomer was 99% e.e. (1S,2R), and the optical purity of the trans-isomer was 91% e.e. (1S,2S). Retention times observed by gas chromatographic analysis [content analysis and cis/trans ratio analysis; column: HR-20M (Shinwa Kako), 0.25 mm ø×30 m, column temperature: 50° C. (0 minute)→+5° C./minute→200° C. (0 minute), injector temperature: 200° C., detector temperature: 250° C., carrier gas: helium, 65 ml/minute, split ratio: 1:50]:
Cis-isomer: 15.0 minutes
Trans-isomer: 14.6 minutes
Retention times observed by gas chromatographic analysis [analysis of the optically active compounds; column: CP-Cyclodextrine-β-236M-19 (Chromatopack), 0.25 mm ø×50 m, column temperature: 85° C. (20 minutes)→+10° C./minute→200° C. (10 minutes), injector temperature: 250° C., detector temperature: 250° C., carrier gas: helium 70 ml/minute, split ratio: 1:100]:
(1R,2R)-Isomer: 21.7 minutes
(1S,2S)-Isomer+(1R,2S)-isomer: 21.9 minutes
(1S,2R)-Isomer: 22.2 minutes

Example 5

Ethyl 2-chloro-2-fluorocyclopropanecarboxylate

Cyclohexane (76.6 g), 2,2'-isopropylidenebis[(4S)-4-tert-butyl-2-oxazoline] (75.8 mg, 0.26 mmol), and copper (I) trifluoromethanesulfonate benzene complex (58.3 mg, 0.23 mmol) were added in an autoclave, and then 1-chloro-1-fluoroethylene (78.9 g, 0.98 mol) was charged under elevated pressure. After the mixed solution was cooled to 10° C., the a mixed solution containing 95% of ethyl diazoacetate (12.0 g, 100 mmol) and cyclohexane (50 g) was charged into the autoclave under elevated pressure over five hours. Cyclohexane (20 ml) was further charged under elevated pressure and stirring was continued at the same temperature for 1 hour, and then the internal pressure was released to give a solution of ethyl 2-chloro-2-fluorocyclopropanecarboxylate in cyclohexane (170.0 g). The content of the ethyl 2-chloro-2-fluoro- cyclopropanecarboxylate was 6.45% (yield based on ethyl diazoacetate: 65.6%), and the ratio of cis-isomer/trans-isomer was 64.6/35.4. The optical purity of the cis-isomer was 99% e.e. (1S,2R), and the optical purity of the trans-isomer was 92% e.e. (1S,2S).

Example 6

Ethyl 2-chloro-2-fluorocyclopropanecarboxylate

Cyclohexane (76.6 g), 2,2'-isopropylidenebis[(4S)-4-tert-butyl-2-oxazoline] (500 mg, 1.7 mmol), and copper (II) trifluoromethanesulfonate (360 mg, 1.0 mmol) were added in an autoclave, and the mixture was cooled to a temperature below −30° C., and then 1-chloro-1-fluoroethylene (80 g, 1.0 mol) was charged under elevated pressure. Phenylhydrazine (0.11 g, 1.0 mmol) was added to this mixture under elevated pressure, and then temperature was raised to 30° C. Then, a mixed solution containing 97.6% of ethyl diazoacetate (11.69 g, 100 mmol) and cyclohexane (50 g) was charged under elevated pressure over five hours. Cyclohexane (20 ml) was further charged under elevated pressure and stirring was continued at the same temperature for 1 hour, and then the internal pressure was released to give a solution of ethyl 2-chloro-2-fluorocyclopropanecarboxylate in cyclohexane (166.7 g). The content of was 3.95% (yield based on ethyl diazoacetate: 39.5%), and the ratio of cis-isomer/trans-isomer was 65.0/35.0. The optical purity of the cis-isomer was 98% e.e. (1S,2R) or more, and the optical purity of the trans-isomer was 94% e.e. (1S,2S).

Example 7

Ethyl 2-chloro-2-fluorocyclopropanecarboxylate n-Heptane (38.3 g), 2,2'-isopropylidenebis[(4S)-4-tert-butyl-2-oxazoline] (162 mg, 0.55 mmol), and copper (II) trifluoromethanesulfonate (180 mg, 0.50 mmol) were added in in an autoclave, and then 1-chloro-1-fluoroethylene (40 g, 0.50 mol) was charged under elevated pressure. After the mixed solution was warmed to 30° C., a mixed solution containing 95% of ethyl diazoacetate (6.0 g, 50 mmol) and n-heptane (25 g) was charged under elevated pressure over five hours. n-Heptane (20 ml) was further charged under elevated pressure and stirring was continued at the same temperature for 1 hour, and then the internal pressure was released to obtain a solution of ethyl 2-chloro-2-fluorocyclopropanecarboxylate in n-heptane (90.0 g). The content of the ethyl 2-chloro-2-fluoro- cyclopropanecarboxylate was 3.73% (yield based on ethyl diazoacetate: 40.3%), and the ratio of cis-isomer/trans-isomer was 64.0/36.0. The optical purity of the cis-isomer was 98% e.e. (1S,2R), and the optical purity of the trans-isomer was 86% e.e. (1S,2S).

Example 8

Ethyl 2-chloro-2-fluorocyclopropanecarboxylate

Cyclohexane (76.6 g), 2,2'-methylenebis[(4S)-4-tert-butyl-2-oxazoline] (293 mg, 1.1 mmol), and copper (II)

trifluoromethanesulfonate (361 mg, 1.0 mmol) were added in an autoclave, and then 1-chloro-1-fluoroethylene (80 g, 1.0 mol) was charged under elevated pressure. After the mixture was warmed to 30° C., a mixed solution containing 95% of ethyl diazoacetate (12.01 g, 100 mmol) and cyclohexane (50 g) was charged under elevated pressure over five hours. Cyclohexane (20 ml) was further charged under elevated pressure and stirring was continued at the same temperature for 1 hour, and then the internal pressure was released to obtain a solution of ethyl 2-chloro-2-fluorocyclopropane-carboxylate in cyclohexane (183.86 g). The content of the ethyl 2-chloro-2-fluorocyclopropanecarboxylate was 4.92% (yield based on ethyl diazoacetate: 54.3%), and the ratio of cis-isomer/trans-isomer was 59.5/40.5. The optical purity of the cis-isomer was 71% e.e. (1S,2R), and the optical purity of the trans-isomer was 19% e.e. (1S,2S).

Example 9

Ethyl 2-chloro-2-fluorocyclopropanecarboxylate

Dichloromethane (38 g), (1R,2R)-1,2-diphenyl-N,N'-bis[2,4,6-trimethylphenyl-methyl]ethylenediamine (715 mg, 1.5 mmol), and copper (II) trifluoromethanesulfonate (180 mg, 0.5 mmol) were added in an autoclave, and then 1-chloro-1-fluoroethylene (40 g, 500 mmol) was charged under elevated pressure. After the mixture was warmed to 30° C., a mixed solution containing 95% of ethyl diazoacetate (6.00 g, 50 mmol) and dichloromethane (50 ml) was charged under elevated pressure over five hours. Dichloromethane (20 ml) was further charged under elevated pressure and stirring was continued at the same temperature for 1 hour, and then the internal pressure was released to obtain and a solution of ethyl 2-chloro-2-fluorocyclopropanecarboxylate in cyclohexane (106.31 g). The content of the ethyl 2-chloro-2-fluorocyclopropanecarboxylate was 3.62% (yield based on ethyl diazoacetate: 46.2%), and the ratio of cis-isomer/trans-isomer was 62.4/37.6. The optical purity of the cis-isomer was 75% e.e. (1S,2R), and the optical purity of the trans-isomer was 73% e.e. (1S,2S).

Industrial Applicability

According to the process of the present invention, optically active halogenated cyclopropane derivatives which are useful for the manufacture of the optically active (1S,2S)-2-fluorocyclopropanecarboxylic acid can be efficiently and stereoselectively prepared.

What is claimed is:
1. A process for preferentially preparing an optically active compound represented by the following general formula (I):

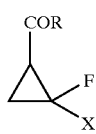

wherein:
the stereochemical configuration at 1-position is S-configuration;
X represents chlorine atom, bromine atom, or iodine atom;
R represents a $C_{1-10}$ alkyloxy group which may have one or more halogen atoms or $C_{1-10}$ alkyloxy groups;
an aralkyloxy group constituted by an aryl group which may have a substituent(s) and a $C_{1-10}$ alkyloxy group;
an aryloxy group having one or more aryl groups which may be substituted;
a $C_{1-10}$ alkylthio group which may have one or more halogen atoms;
an aralkylthio group constituted by an aryl group which may have a substituent(s) and a $C_{1-10}$ alkylthio group;
amino group; or
a substituted amino group which has one or more substituents selected from the group consisting of a $C_{1-10}$ alkyl group, an aryl group which may be substituted, an aralkyl group constituted by an aryl group which have a substituent(s) and a $C_{1-10}$ alkyl group, and an acyl group;
provided that substituents of the substituted aryl groups are selected from the group consisting of a halogen atom, a $C_{1-10}$ alkyl group, a $C_{1-10}$ halogenoalkyl group, a $C_{1-10}$ alkyloxy group, a carbamoyl group which may be substituted, hydroxyl group, nitro group, cyano group, and an amino group which may be substituted;
which process comprises reacting a compound represented by the formula: $N_2CHCOR$ wherein R is the same as that defined above with a compound represented by the formula: $CH_2=CXF$ wherein X is the same as that defined above in the presence of a catalyst obtainable from a copper source, and at least one chiral ligand selected from the group consisting of an oxazoline-type ligand of the formula:

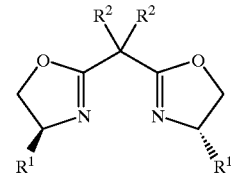

wherein $R^1$ represents a lower alkyl group having 1 to 5 carbon atoms or phenyl group which may be substituted, and the stereochemistry of each asymmetric carbon bound by $R^1$ is S-configuration and $R^2$ represents hydrogen atom or methyl group, and
a diamine-type ligand of the formula:

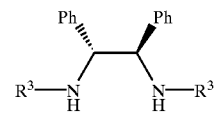

wherein $R^3$ represents benzyl group, 2,4,6-trimethyiphenylmethyl group, or diphenylmethyl group, and the stereochemistry of each asymmetric carbon atom bound by the phenyl group is R-configuration.
2. The process according to claim 1 wherein the copper source is at least one substance selected from the group consisting of copper (I) trifluoromethanesulfonate [$CuOSO_2CF_3$] and copper (II) trifluoromethanesulfonate [$Cu(OSO_2CF_3)_2$].
3. The process according to claim 1 wherein X is chlorine atom or bromine atom.
4. The process according to claim 1 wherein R is $C_{1-10}$ alkyloxy group.

5. The process according to claim 1 wherein R is ethoxy group.

6. A process for preparing a (1S,2S)-2-fluorocyclopropanecarboxylic acid derivative, which comprises:
(A) preparing a stereoisomer of the compound of the general formula (I) according to the process of claim 1; and
(B) subjecting the resulting stereoisomer to dehalogenation to replace X of the stereoisomer with hydrogen atom to prepare a (1S,2S)-2-fluorocyclopropanecarboxylic acid derivative.

7. A process for preparing a (1S,2S)-2-fluorocyclopropanecarboxylic acid derivative which comprises subjecting a stereoisomer of the compound of the general formula (I) prepared according to the reaction process defined by claim 1 to dehalogenation reaction without purification or isolation to replace X of the stereoisomer with hydrogen atom to prepare a (1S,2S)-2-fluorocyclopropanecarboxylic acid derivative.

8. The process according to claim 1 wherein the oxazoline-type ligand comprises 2,2'-methylenebis[(4S)-4-tert-butyl-2-oxazoline].

9. The process according to claim 1 wherein the oxazoline-type ligand comprises 2,2'-isopropylidene-bis-[(4S)-4-tert-butyl-2-oxazoline].

10. The process according to claim 1 wherein the oxazoline-type ligand comprises 2,2'-methylenebis[(4S)-4-isopropyl-2-oxazoline] and 2,2'-isopropylidenebis[(4S)-4-isopropyl-2-oxazoline].

11. The process according to claim 1 wherein the oxazoline-type ligand comprises 2,2'-isopropylidenebis[(4S)-4-benzyl-2-oxazoline].

12. The process according to claim 1 wherein the diamine-type ligand comprises (1R,2R)-1,2-diphenyl-N,N'-bis[2,4,6-trimethylphenylmethyl]-ethylenediamine.

13. The process according to claim 1 wherein the diamine-type ligand comprises (1R,2R)-1,2-diphenyl-N,N'-bisbenzylethylenediamine.

14. A process for preferentially preparing an optically active compound represented by the following general formula (I):

wherein:
the stereochemical configuration at 1-position is S-configuration;
X represents chlorine atom, bromine atom, or iodine atom;
R represents a $C_{1-10}$ alkyloxy group which may have one or more halogen atoms or $C_{1-10}$ alkyloxy groups;
an aralkyloxy group constituted by an aryl group which may have a substituent(s) and a $C_{1-10}$ alkyloxy group;
an aryloxy group having one or more aryl groups which may be substituted;
a $C_{1-10}$ alkylthio group which may have one or more halogen atoms;
an aralkylthio group constituted by an aryl group which may have a substituent(s) and a $C_{1-10}$ alkylthio group;
amino group; or
a substituted amino group which has one or more substituents selected from the group consisting of a $C_{1-10}$ alkyl group, an aryl group which may be substituted, an aralkyl group constituted by an aryl group which have a substituent(s) and a $C_{1-10}$ alkyl group, and an acyl group;
provided that substituents of the substituted aryl groups are selected from the group consisting of a halogen atom, a $C_{1-10}$ alkyl group, a $C_{1-10}$ halogenoalkyl group, a $C_{1-10}$ alkyloxy group, a carbamoyl group which may be substituted, hydroxyl group, nitro group, cyano group, and an amino group which may be substituted;
which process comprises reacting a compound represented by the formula: $N_2CHCOR$ wherein R is the same as that defined above with a compound represented by the formula: $CH_2=CXF$ wherein X is the same as that defined above in the presence of a catalyst component copper substance, and at least one chiral ligand selected from the group consisting of an oxazoline-type ligand of the formula:

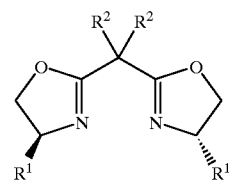

wherein $R^1$ represents a lower alkyl group having 1 to 5 carbon atoms or phenyl group which may be substituted, and the stereochemistry of each asymmetric carbon bound by $R^1$ is S-configuration and $R^2$ represents hydrogen atom or methyl group, and a diamine-type ligand of the formula:

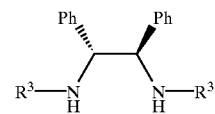

wherein $R^3$ represents benzyl group, 2,4,6-trimethylphenylmethyl group, or diphenylmethyl group, and the stereochemistry of each asymmetric carbon atom bound by the phenyl group is R-configuration.

15. The process according to claim 1 wherein the at least one chiral ligand is an oxazoline-type ligand of the formula:

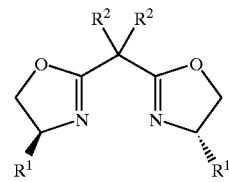

wherein $R^1$ represents a lower alkyl group having 1 to 5 carbon atoms or phenyl group which may be substituted, and the stereochemistry of each asymmetric carbon bound by $R^1$ is S-configuration and $R^2$ represents hydrogen atom or methyl group.

16. The process according to claim 1 wherein the at least one chiral ligand is a diamine-type ligand of the formula:

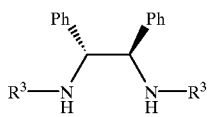

wherein R³ represents benzyl group, 2,4,6-trimethyiphenylmethyl group, or diphenylmethyl group, and the stereochemistry of each asymmetric carbon atom bound by the phenyl group is R-configuration.

17. The process according to claim 14 wherein the at least one chiral ligand is an oxazoline-type ligand of the formula:

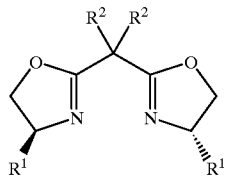

wherein R¹ represents a lower alkyl group having 1 to 5 carbon atoms or phenyl group which may be substituted, and the stereochemistry of each asymmetric carbon bound by R¹ is S-configuration and R² represents hydrogen atom or methyl group.

18. The process according to claim 14 wherein the at least one chiral ligand is a diamine-type ligand of the formula:

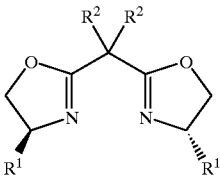

wherein R³ represents benzyl group, 2,4,6-trimethyiphenylmethyl group, or diphenylmethyl group, and the stereochemistry of each asymmetric carbon atom bound by the phenyl group is R-configuration.

* * * * *

UNITED STATES PATENT AND TRADEMARK OFFICE
CERTIFICATE OF CORRECTION

PATENT NO. : 6,596,898 B2
DATED : July 22, 2003
INVENTOR(S) : T. Ebata et al.

It is certified that error appears in the above-identified patent and that said Letters Patent is hereby corrected as shown below:

Column 21,
Line 9, "trimethyiphenylmethyl" should be -- trimethylphenylmethyl --.

Column 22,
Line 10, " 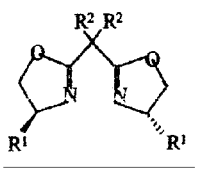 "should be 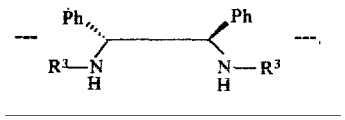 --.

Line 19, "trimethyiphenylmethyl" should be -- trimethylphenylmethyl --.

Signed and Sealed this

Thirty-first Day of August, 2004

JON W. DUDAS
*Director of the United States Patent and Trademark Office*